United States Patent
Hu et al.

(10) Patent No.: US 11,707,528 B2
(45) Date of Patent: Jul. 25, 2023

(54) MANNOSE-BASED MRNA TARGETED DELIVERY SYSTEM AND USE THEREOF

(71) Applicant: Shenzhen Rhegen Biotechnology Co., Ltd.

(72) Inventors: Yong Hu, Shenzhen (CN); Miaomiao Zhang, Shenzhen (CN)

(73) Assignee: ShenZhen Rhegen Biotechnology Co., Ltd., Shenzhen (CN)

( * ) Notice: Subject to any disclaimer, the term of this patent is extended or adjusted under 35 U.S.C. 154(b) by 0 days.

(21) Appl. No.: 17/559,620

(22) Filed: Dec. 22, 2021

(65) Prior Publication Data

US 2022/0118099 A1  Apr. 21, 2022

Related U.S. Application Data

(63) Continuation of application No. PCT/CN2020/123993, filed on Oct. 27, 2020.

(30) Foreign Application Priority Data

Jul. 1, 2020  (CN) .......................... 202010629898.4

(51) Int. Cl.
*A61K 47/54* (2017.01)
*A61K 39/385* (2006.01)
*C07H 5/00* (2006.01)
*C07H 5/06* (2006.01)
*A61K 39/00* (2006.01)

(52) U.S. Cl.
CPC .......... *A61K 47/549* (2017.08); *A61K 39/385* (2013.01); *C07H 5/00* (2013.01); *C07H 5/06* (2013.01); *A61K 2039/53* (2013.01)

(58) Field of Classification Search
None
See application file for complete search history.

(56) References Cited

U.S. PATENT DOCUMENTS

| | | | |
|---|---|---|---|
| 6,537,749 B2 | 3/2003 | Kuimelis et al. | |
| 8,106,022 B2* | 1/2012 | Manoharan | A61K 31/7004 536/18.7 |
| 8,828,956 B2* | 9/2014 | Manoharan | A61K 31/7088 536/23.1 |
| 9,271,996 B2 | 3/2016 | De et al. | |
| 9,295,689 B2 | 3/2016 | De et al. | |
| 9,506,030 B2 | 11/2016 | Bhat | |
| 9,512,456 B2 | 12/2016 | Wang et al. | |
| 9,867,882 B2 | 1/2018 | Manoharan et al. | |
| 10,155,029 B2 | 12/2018 | Chakraborty et al. | |
| 10,806,791 B2 | 10/2020 | Manoharan et al. | |
| 10,844,379 B2 | 11/2020 | Prakash et al. | |
| 2010/0055761 A1 | 3/2010 | Seed et al. | |
| 2011/0124520 A1 | 5/2011 | Love et al. | |
| 2013/0022538 A1 | 1/2013 | Rossi et al. | |
| 2016/0209421 A1 | 7/2016 | Suga | |
| 2019/0085331 A1 | 3/2019 | Hadwiger et al. | |
| 2019/0160176 A1 | 5/2019 | Heyes et al. | |
| 2019/0343933 A1 | 11/2019 | Horscroft et al. | |
| 2020/0085944 A1* | 3/2020 | Heidenreich | A61K 39/0011 |
| 2021/0017214 A1 | 1/2021 | Albaek et al. | |
| 2021/0054018 A1 | 2/2021 | Murray et al. | |
| 2022/0090055 A1 | 3/2022 | Krauss et al. | |

FOREIGN PATENT DOCUMENTS

| | | |
|---|---|---|
| CN | 1297907 A | 6/2001 |
| CN | 1347903 A | 5/2002 |
| CN | 101558081 A | 10/2009 |
| CN | 103282502 A | 9/2013 |
| CN | 103547272 A | 1/2014 |
| CN | 104189897 A | 12/2014 |
| CN | 105658797 A | 6/2016 |
| CN | 105899666 A | 8/2016 |
| CN | 107530436 A | 1/2018 |
| CN | 108026527 A | 5/2018 |
| CN | 108271387 A | 7/2018 |
| CN | 108949772 A | 12/2018 |
| CN | 110637086 A | 12/2019 |
| CN | 111041025 A | 4/2020 |
| EP | 2652134 B1 | 3/2017 |
| EP | 2970351 B1 | 9/2017 |
| EP | 2991661 B1 | 3/2019 |
| EP | 3546579 A1 | 10/2019 |

(Continued)

OTHER PUBLICATIONS

Jayaprakash KN, Peng CG, Butler D, Varghese JP, Maier MA, Rajeev KG, Manoharan M. Non-nucleoside building blocks for copper-assisted and copper-free click chemistry for the efficient synthesis of RNA conjugates. Organic Letters. Dec. 3, 2010;12(23):5410-3. (Year: 2010).*

Van Hoecke L, Roose K. How mRNA therapeutics are entering the monoclonal antibody field. Journal of Translational Medicine. Dec. 2019;17(1):1-4. (Year: 2019).*

Craig K, Abrams M, Amiji M. Recent preclinical and clinical advances in oligonucleotide conjugates. Expert opinion on drug delivery. Jun. 3, 2018;15(6):629-40. (Year: 2018).*

(Continued)

*Primary Examiner* — Robert M Kelly

(74) *Attorney, Agent, or Firm* — Wilson Sonsini Goodrich & Rosati

(57) ABSTRACT

The present invention provides a mannose-based mRNA targeted delivery system and use thereof. The mRNA can encode one or more target polypeptides and contains at least one mannose modification. The technical solution of the present invention modifies the mRNA molecule with a mannose, so that the mRNA can be directly and efficiently coupled with the mannose, and the targeted delivery of the mRNA is realized without the need for a carrier.

10 Claims, 9 Drawing Sheets

Specification includes a Sequence Listing.

(56) References Cited

FOREIGN PATENT DOCUMENTS

| | | |
|---|---|---|
| EP | 2971010 B1 | 6/2020 |
| JP | 2006517512 A | 7/2006 |
| JP | 2018537399 A | 12/2018 |
| WO | WO-2014160129 A2 | 10/2014 |
| WO | WO-2014160129 A3 | 12/2014 |
| WO | WO-2017212009 A1 | 12/2017 |
| WO | WO-2018104538 A1 | 6/2018 |
| WO | WO-2018140362 A1 | 8/2018 |
| WO | WO-2018168999 A1 | 9/2018 |
| WO | WO-2019063843 A1 | 4/2019 |
| WO | WO-2019077001 A1 * | 4/2019 ......... A61K 31/7088 |
| WO | WO-2020056370 A9 * | 5/2020 ......... A61K 31/7115 |
| WO | WO-2020093053 A1 | 5/2020 |
| WO | WO-2021030778 A1 | 2/2021 |
| WO | WO-2021121173 A1 | 6/2021 |
| WO | WO-2021139474 A1 | 7/2021 |
| WO | WO-2022000884 A1 | 1/2022 |

OTHER PUBLICATIONS

Andries O, Mc Cafferty S, De Smedt SC, Weiss R, et al. N1-methylpseudouridine-incorporated mRNA outperforms pseudouridine-incorporated mRNA by providing enhanced protein expression and reduced immunogenicity in mammalian cell lines and mice. Journal of Controlled Release. Nov. 10, 2015;217:337-44. (Year: 2015).*

Ikeda Y, Kubota D, Nagasaki Y. Simple solid-phase synthesis and biological properties of carbohydrate-oligonucleotide conjugates modified at the 3'-terminus. Bioconjugate chemistry. Sep. 15, 2010;21(9):1685-90. (Year: 2010).*

Shin H, Park SJ, Yim Y, Kim J, Choi C, Won C, Min DH. Recent advances in RNA therapeutics and RNA delivery systems based on nanoparticles. Advanced Therapeutics. Nov. 2018; 1(7):1800065 (Year: 2018).*

Bai, et al. (白宇超等) Research Progress of Targeted Drug Delivery System Based on Carbohydrate Compounds (基于糖类化合物靶向药物载体的研究进展). Chemical World (化学党界). vol. 59, No. 7, May 25, 2018. pp. 393-399 (English Abstract).

International search report with written opinion dated Mar. 25, 2021 for PCT/CN2020/123993 (English Translation).

Jung, et al. CpG oligonucleotide and α-D-mannose conjugate for efficient delivery into macrophages. Applied Biological Chemistry. Published Sep. 11, 2016. 59(5):759-763.

Zhao, et al. Synthesis and characterization of mannosylated oligoribonucleotides. Carbohydr Res. Nov. 2, 2009;344(16):2137-2143. doi: 10.1016/j.carres.2009.08.033. Epub Aug. 31, 2009.

Baenziger et al. Galactose and N-acetylgalactosamine-specific endocytosis of glycopeptides by isolated rat hepatocytes. Cell 22:611-620 (1980).

Connolly et al. Binding and endocytosis of cluster glycosides by rabbit hepatocytes. Evidence for a short-circuit pathway that does not lead to degradation. J. Biol. Chem. 257:939-945 (1982).

Co-pending U.S. Appl. No. 17/843,162, inventors Hu; Yong et al., filed on Jun. 17, 2022.

European search report and opinion dated Oct. 4, 2022 for EP Application No. 20902709.3.

Fumoto, et al. Methods for Evaluating the Stimuli-Responsive Delivery of Nucleic Acid and Gene Medicines. Chem Pharm Bull (Tokyo). 2017;65(7):642-648. doi: 10.1248/cpb.c17-00096.

Huang, Y. Asialoglycoprotein Receptor and Its Application in Liver-targeted Drug Delivery. Jun. 2015. Progress in Biochemistry and Biophysics 42(6):501-510. DOI:10.16476/j.pibb.2015.0028 (English Abstract p. 10).

Huang Y. Preclinical and Clinical Advances of GalNAc-Decorated Nucleic Acid Therapeutics. Mol Ther Nucleic Acids. Mar. 17, 2017;6:116-132. doi: 10.1016/j.omtn.2016.12.003. Epub Dec. 10, 2016.

International search report with written opinion dated Mar. 8, 2021 for PCT/CN2020/135203 (English Translation).

International search report with written opinion dated Mar. 17, 2021 for PCT/CN2020/136010 (English Translation).

Janas, et al. Selection of GalNAc-conjugated siRNAs with limited off-target-driven rat hepatotoxicity. Nat Commun. Feb. 19, 2018;9(1):723. doi: 10.1038/s41467-018-02989-4.

Javanbakht, et al. Liver-Targeted Anti-HBV Single-Stranded Oligonucleotides with Locked Nucleic Acid Potently Reduce HBV Gene Expression In Vivo. Mol Ther Nucleic Acids. Jun. 1, 2018;11:441-454. doi: 10.1016/j.omtn.2018.02.005. Epub Feb. 23, 2018.

Kershaw, et al. Splint ligation of RNA with T4 Dna ligase. Methods Mol Biol. 2012;941:257-269. doi: 10.1007/978-1-62703-113-4_19.

Nair et al. Multivalent N-acetylgalactosamine-conjugated siRNA localizes in hepatocytes and elicits robust RNAi-mediated gene silencing. J Am Chem Soc. 136(49):16958-16961 (2014).

Office action dated Feb. 20, 2021 for CN Application No. 201911300610.2 (English Translation).

Office action dated Mar. 11, 2021 for CN Application No. 202010027183.1 (English Translation).

Office action dated Apr. 19, 2021 for CN Application No. 201911300610.2 (English Translation).

Office action dated Aug. 18, 2021 for CN Application No. 202010027183.1 (English Translation).

Office action dated Oct. 14, 2022 for U.S. Appl. No. 17/693,173.

Springer, et al. GalNAc-siRNA Conjugates: Leading the Way for Delivery of RNAi Therapeutics. Nucleic Acid Ther. Jun. 2018;28(3):109-118. doi: 10.1089/nat.2018.0736. Epub May 24, 2018.

Stefanescu, et al. Epitope structure of the carbohydrate recognition domain of asialoglycoprotein receptor to a monoclonal antibody revealed by high-resolution proteolytic excision mass spectrometry. J Am Soc Mass Spectrom. Jan. 2011;22(1):148-157. doi: 10.1007/s13361-010-0010-y. Epub Jan. 20, 2011.

Wang, et al. Optimization of the Linker Length of Mannose-Cholesterol Conjugates for Enhanced mRNA Delivery to Dendritic Cells by Liposomes. Front Pharmacol. Sep. 5, 2018;9:980. doi: 10.3389/fphar.2018.00980. eCollection 2018.

Zhao, et al. RNA delivery biomaterials for the treatment of genetic and rare diseases. Biomaterials. Oct. 2019;217:119291. doi: 10.1016/j.biomaterials.2019.119291. Epub Jun. 20, 2019.

Bennett, et al. Control of mucin-type O-glycosylation: a classification of the polypeptide GalNAc-transferase gene family. Glycobiology. Jun. 2012;22(6):736-756. doi: 10.1093/glycob/cwr182. Epub Dec. 18, 2011.

European search report and opinion dated Jan. 31, 2023 for EP Application No. 20942695.6.

Irache, et al. Mannose-targeted systems for the delivery of therapeutics. Expert Opin Drug Deliv. Jun. 2008;5(6):703-724. doi: 10.1517/17425247.5.6.703.

Mochizuki, et al. One-pot preparation of mRNA/cDNA display by a novel and versatile puromycin-linker DNA. ACS Comb Sci. Sep. 12, 2011;13(5):478-485. doi: 10.1021/co2000295. Epub Jul. 28, 2011.

Office action dated Feb. 21, 2023 for U.S. Appl. No. 17/693,173.

Pichon, et al. Mannosylated and histidylated LPR technology for vaccination with tumor antigen mRNA. Methods Mol Biol. 2013;969:247-274. doi: 10.1007/978-1-62703-260-5_16.

Prieve, et al. Targeted mRNA Therapy for Ornithine Transcarbamylase Deficiency. Mol Ther. Mar. 7, 2018;26(3):801-813. doi: 10.1016/j.ymthe.2017.12.024. Epub Jan. 4, 2018.

Spinelli, et al. Glycoclusters on oligonucleotide and PNA scaffolds: synthesis and applications. Chem Soc Rev. Jun. 7, 2013;42(11):4557-4573. doi: 10.1039/c2cs35406c. Epub Dec. 19, 2012.

Yan, et al. Glycotargeting to improve cellular delivery efficiency of nucleic acids. Glycoconj J. Apr. 2007;24(2-3):107-123. doi: 10.1007/s10719-006-9023-y. Epub Feb. 1, 2007.

* cited by examiner

SEQUENCE LISTING

<160> NUMBER OF SEQ ID NOS: 1

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1
aaaaaaaaaa aaaaaaaaaa aaaaaaaaaa                    30

MANNOSE-BASED MRNA TARGETED DELIVERY SYSTEM AND USE THEREOF

CROSS REFERENCE TO RELATED APPLICATIONS

This application is a continuation application of International Application No. PCT/CN2020/123993, filed on Oct. 27, 2020, which claims the priority of Chinese patent application filed to the China National Intellectual Property Administration on Jul. 1, 2020, with an application number of 2020106298984, titled "Mannose-based mRNA targeted delivery system and use thereof", each of which is incorporated herein by reference in its entirety.

SEQUENCE LISTING

The instant application contains a Sequence Listing which has been submitted electronically in ASCII format and is hereby incorporated by reference in its entirety. Said ASCII copy created on Dec. 22, 2021, is named 60943_705_301 SL.txt and is 583 bytes in size.

TECHNICAL FIELD

The present invention belongs to the field of biotechnology, and more specifically relates to a mannose-based mRNA targeted delivery system and use thereof.

BACKGROUND

Lectin receptors are a class of glycoproteins, glycolipids or glycoconjugates distributed on the surface of the cell membrane, which can specifically recognize and bind to a part of glycosyls. The mannose receptor is the most important and highly efficient endocytic lectin receptor, whose function comprises eliminating endogenous molecules, promoting antigen presentation, and regulating cell activation and trafficking, and is also closely related to the immune escape and metastasis of tumors. It is mainly expressed in macrophages, dendritic cells and tumor cells, and can specifically recognize mannose glycosyl molecules. As the most promising targeted group, mannosyl has many advantages such as non-toxicity, non-immunogenicity, good biocompatibility and biodegradability, and can be widely used in glycosylation modification of nucleic acid drug delivery systems.

Liposome is a bilayer vesicle having a structure similar to a biological membrane, and nanoliposome is a liposome structure with a particle size of less than 100 nm which is the most classic nano-targeted drug delivery carrier. In the prior art, mannose has been coupled to nanoliposomes to improve their targeting.

However, in the process of preparing nanoliposomes, a large amount of organic solvents that are harmful to the human body are used, resulting in residual toxic organic solvents. Moreover, there are problems with these traditional nanoliposome preparation methods, such as low encapsulation rates, easy rupture of liposome membranes, poor stability, insufficient storage stability, difficulty in achieving large-scale production, and high cost. Therefore, if mannose can be directly coupled to nucleic acid drugs, nanoliposomes can be omitted.

SUMMARY

In view of the above, the purpose of the present invention is to provide an mRNA modification method, by which the modification of mature mRNA molecules with mannose can be realized, so that the mRNAs can be directly and efficiently coupled with mannose, and thus the targeted delivery of the mRNAs can be carried out without the need for a carrier.

To achieve the above-mentioned purpose of the invention, the present invention provides the following technical solutions:

The present invention provides an mRNA-mannose conjugate comprising:

an mRNA encoding a polypeptide, the structure of the mRNA comprising at least one 5' cap structure, a 5' UTR with at least one Kozak sequence, a 3' UTR and a polyA tail, the mRNA being composed of uridine, cytidine, adenosine, guanosine and/or chemically modified nucleosides thereof, and the terminus of the mRNA being modified with at least one mannose.

Preferably, the chemically modified nucleoside is one or more selected from the group consisting of pyridin-4-one ribonucleoside, 5-aza-uridine, 2-thio-5-aza-uridine, 2-thiouridine, 4-thiopseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyl uridine, 1-taurinomethyl-pseudouridine, 5-taurinomethyl-2-thio-uridine, 1-taurinomethyl-4-thio-uridine, 5-methyl-uridine, 1-methyl pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methylcytidine, N4-acetylcytidine, 5-formyl cytidine, N4-methyl cytidine, 5-hydroxymethyl cytidine, 1-methyl pseudoisocytidine, pyrrolo-cytidine, pyrrolo-pseudoisocytidine, 2-thiocytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine-methyladenosine, N6-methyladenosine, N6-isopentenyladenosine, N6-(cis-hydroxyisopentenyl)adenosine, 2-methylthio-N6-(cis-hydroxyisopentenyl)adenosine, N6-glycylcarbamoyladenosine, N6-threonylcarbamoyladenosine, 2-methylthio-N6-threonylcarbamoyladenosine, N6,N6-dimethyladenosine, 7-methyladenine, 2-methylthio-adenine, 2-methoxy-adenosine, inosine, 1-methyl-inosine, Y nucleoside, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine and N2,N2-dimethyl-6-thio-guanosine.

Preferably, the at least one 5' cap structure is one or more selected from the group consisting of Cap0, Cap1, ARCA, inosine, N1-methyl-guanosine, 2'-fluoro-guanosine, 7-deaza-guanosine, 8-oxo-guanosine, 2-amino-guanosine, LNA-guanosine, 2-azido-guanosine, 7-methyl-guanosine- 5'-triphosphate-5'-adenosine, guanosine-5'-triphosphate-5'-adenosine, 7-methyl-guanosine-5'-triphosphate-5'-guanosine, guanosine-5'-triphosphate-5'-guanosine, and 7-methyl-guanosine-5'-triphosphate-5'-2-methoxyadenine-guanosine.

Preferably, the terminus of the mRNA is modified with an amino group, and at least one mannose is linked to the mRNA through the amino group.

The present invention also provides a kit, comprising: an mRNA, the 3' end of the mRNA being labeled with an amino group; and a mannose, the mannose and the amino group being covalently linked through an isourea bond.

The present invention also provides a kit, comprising: an mRNA precursor comprising a coding sequence encoding a specific protein;

a polyadenylic acid, the 3' end of the polyadenylic acid being labeled with an amino group;

a mannose, the mannose and the amino group being covalently linked through an isourea bond; and a ligase, the ligase being used for linking the mRNA precursor and the polyadenylic acid.

The present invention also provides a kit, comprising: an mRNA precursor comprising a coding sequence encoding a specific protein;

a conjugate of a polyadenylic acid with an amino group at the 3' end and a mannose; and a ligase, the ligase being used for linking the mRNA precursor and the polyadenylic acid.

Preferably, the ligase comprises a T4 RNA ligase.

Preferably, the ligase comprises a T4 DNA ligase, and the kit further comprises a splint DNA for linking the mRNA precursor and the polyadenylic acid.

The present invention also provides a preparation method of an mRNA composition, comprising:

synthesizing a polyadenylic acid of which the 3' end is labeled with an amino group;

linking the 3' end of the mRNA precursor to the 5' end of the polyadenylic acid to obtain an mRNA of which the 3' end is labeled with an amino group; and linking the mRNA of which the 3' end is labeled with an amino group to a mannose to prepare and obtain the mRNA composition.

The present invention also provides a preparation method of an mRNA composition, comprising:

synthesizing a polyadenylic acid of which the 3' end is labeled with an amino group;

linking the polyadenylic acid to a mannose through an isourea bond to obtain a polyadenylic acid-mannose conjugate;

linking the polyadenylic acid-mannose conjugate to an mRNA precursor to prepare and obtain the mRNA composition.

The seventh aspect of the present invention further presents an mRNA drug comprising an mRNA-mannose conjugate.

The present invention further presents a pharmaceutical composition, comprising an mRNA-mannose conjugate and a pharmaceutically acceptable excipient.

The present invention further presents a use of the mRNA-mannose conjugate or the above-mentioned pharmaceutical composition in the preparation of a medicament for expressing a target polypeptide in a mammalian subject.

Compared with the prior art, the present invention has the following beneficial effects: the technical solution of the present invention allows modifying mature mRNA molecules with a mannose, so that the mRNA can be directly and efficiently coupled with the mannose, and then targeted delivery of the mRNA can be achieved without using a nanoliposome as a carrier.

DETAILED DESCRIPTION OF THE INVENTION

The present invention will be further illustrated below in combination with examples and accompanying drawings.

Figure 1:
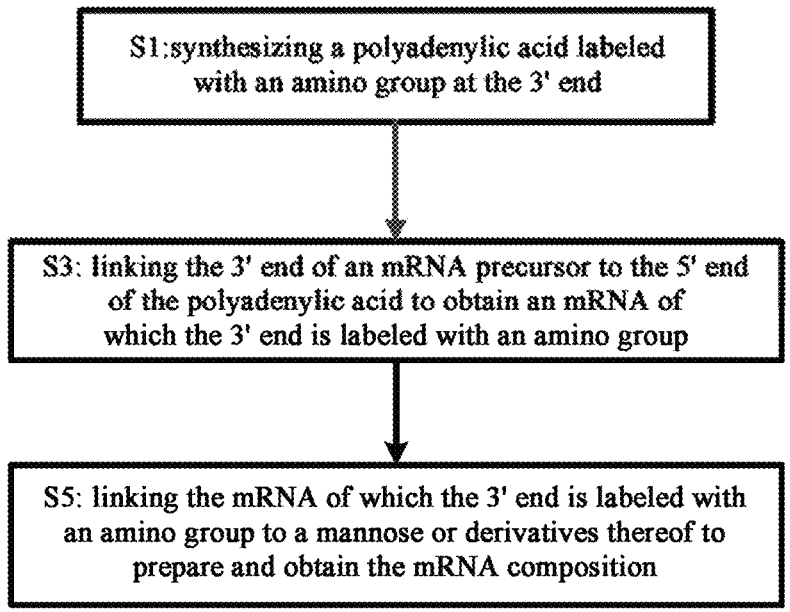
FIG. 1 is a schematic flow chart showing an example of the preparation method of the mRNA composition according to the present invention (for linking a mannose in the terminal reaction)

The present invention presents a preparation method of an mRNA composition, see FIG. 1, comprising:

S1, synthesizing a polyadenylic acid labeled with an amino group at the 3' end;

S3, linking the 3' end of an mRNA precursor to the 5' end of the polyadenylic acid to obtain an mRNA of which the 3' end is labeled with an amino group; and S5, linking the mRNA of which the 3' end is labeled with an amino group to a mannose to prepare and obtain the mRNA composition.

The technical solution of the present invention allows modifying the 3' end of an mRNA with an amino group, so that the mRNA is linked to a mannose through an isourea bond of the amino group to obtain an mRNA-mannose conjugate. The resulting mRNA-mannose conjugate is able to target specific cells without the need for a carrier, which simplifies the preparation process of mRNA drugs and greatly improves the level of development and utilization of mRNA drugs.

In the practice of the present invention, it will be appreciated that the raw materials obtained from or used by the preparation method comprise a polyadenylic acid of which the 3' end is labeled with an amino group, an mRNA precursor, a mannose and a ligase, and these materials can be present in the form of a kit, so that a kit is obtained comprising: an mRNA precursor, the mRNA precursor comprising a coding sequence encoding a specific protein; a polyadenylic acid, the 3' end of the polyadenylic acid being labeled with an amino group; a mannose, the mannose and the amino group being covalently linked through an isourea bond; and a ligase, the ligase being used for linking the mRNA precursor and the polyadenylic acid.

In a further aspect, the intermediate product obtained from the preparation method is an mRNA of which the 3' end is labeled with an amino group, so that a kit can be obtained based on the intermediate product, comprising: an mRNA, the 3' end of the mRNA being labeled with an amino group; and a mannose, the mannose and the amino group being covalently linked through an isourea bond. The process of preparing an mRNA-mannose conjugate with the kit is simpler and convenient to use.

Specifically, the chemical formula of the amino group is —$NH_2$, nevertheless the present invention is not limited to the use of —$NH_2$, any primary amine with the general formula $RNH_2$ can be used, and secondary amines with the general formula $R_2NH$ can be generated.

Specifically, the length of the polyadenylic acid synthesized can be in a range of 1 to 300 bp. The polyadenylic acid is usually the polyA tail sequence of an mRNA. When the polyA tail sequence of an mRNA is too long, the polyadenylic acid can also be a part of the polyA tail sequence, and it will be appreciated that the length of the polyadenylic acid can be the length of any part of the polyA tail sequence. The mRNA precursor is a part of an mRNA that does not comprise the polyadenylic acid sequence, and the mRNA precursor and the polyadenylic acid constitute a complete mRNA sequence. The mRNA has at least one 5' cap structure, a 5' non-coding region (UTR) with at least one Kozak sequence, a 3' non-coding region (UTR), and an open reading frame (ORF), etc. in addition to the polyA tail, and the mRNA is composed of uridine, cytidine, adenosine, guanosine and/or chemically modified nucleosides thereof.

More specifically, the chemically modified nucleoside is one or more selected from the group consisting of pyridin-4-one ribonucleoside, 5-aza-uridine, 2-thio-5-aza-uridine, 2-thiouridine, 4-thiopseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyl uridine, 1-taurinomethyl-pseudouridine, 5-taurinomethyl-2-thio-uridine, 1-taurinomethyl-4-thio-uridine, 5-methyl-uridine, 1-methyl pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methylcytidine, N4-acetylcytidine, 5-formyl cytidine, N4-methyl cytidine, 5-hydroxymethyl cytidine, 1-methyl pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine-methyladenosine, N6-methyladenosine, N6-isopentenyladenosine, N6-(cis-hydroxyisopentenyl)adenosine, 2-methylthio-N6-(cis-hydroxyisopentenyl)adenosine, N6-glycylcarbamoyladenosine, N6-threonylcarbamoyladenosine, 2-methylthio-N6-threonylcarbamoyladenosine, N6,N6-dimethyladenosine, 7-methyladenine, 2-methylthio-adenine, 2-methoxy-adenosine, inosine, 1-methyl-inosine, Y nucleoside, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine and N2,N2-dimethyl-6-thio-guanosine.

More specifically, the at least one 5' cap structure is one or more selected from the group consisting of Cap0, Cap1, ARCA, inosine, N1-methyl-guanosine, 2'-fluoro-guanosine, 7-deaza-guanosine, 8-oxo-guanosine, 2-amino-guanosine, LNA-guanosine, 2-azido-guanosine, 7-methyl-guanosine-5'-triphosphate-5'-adenosine, guanosine-5'-triphosphate-5'-adenosine, 7-methyl-guanosine-5'-triphosphate-5'-guanosine, guanosine-5'-triphosphate-5'-guanosine, and 7-methyl-guanosine-5'-triphosphate-5'-2-methoxyadenine-guanosine. The 5' cap structure can improve the stability of mRNAs.

Unlike plasmid DNAs and viral vectors, mRNAs are immediately translated once they enter the cytoplasm from the outside of cells, and do not need to be integrated into the host genome, avoiding the risk of insertion of gene mutations, moreover, exogenous mRNAs entering cells can be completely degraded by physiological metabolism. Furthermore, the production of mRNAs is simple and low-cost, which greatly shortens the cycle of new drug development and reduces its cost, making mRNA drugs have great advantages.

In one aspect, the problem of instability for mRNA drugs needs to be solved, and the activity of exogenous mRNAs can be prolonged by chemically modifying mRNAs and regulating the structural elements related to the translation and metabolism of mRNAs. Another important aspect is how to enable the modified mRNAs to enter specific cells and tissues of the body. The present invention obtains an mRNA drug by linking the 3' end of an mRNA molecule to a mannose, and achieves tissue-specific delivery of the mRNA by interacting with the mannose receptor on macrophages, thereby increasing the potency of the mRNA drug molecule.

Figure 2:
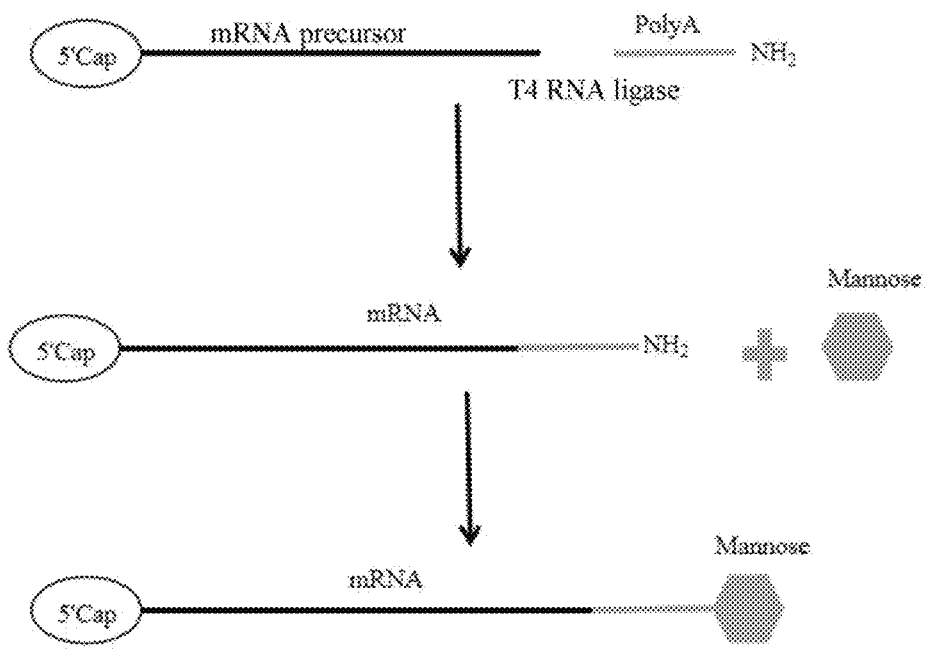
FIG. 2 is a schematic diagram showing the preparation process of the mRNA-mannose conjugate independent of a "splint" DNA in an example of the preparation method of the mRNA composition according to the present invention (for linking a mannose in the terminal reaction)

Optionally, referring to FIG. 2, FIG. 2 is an approach of the preparation method of the mRNA composition in this example. The synthesized polyadenylic acid of which the 3' end is labeled with an amino group and the mRNA precursor are linked by a T4 RNA ligase to form a mature mRNA, and then the resulting mature mRNA is linked with a mannose to obtain an mRNA-mannose conjugate.

Specifically, the ligase in the kit corresponding to the materials obtained from or used in the preparation method in the examples of the present invention comprises T4 RNA ligase.

Figure 3:
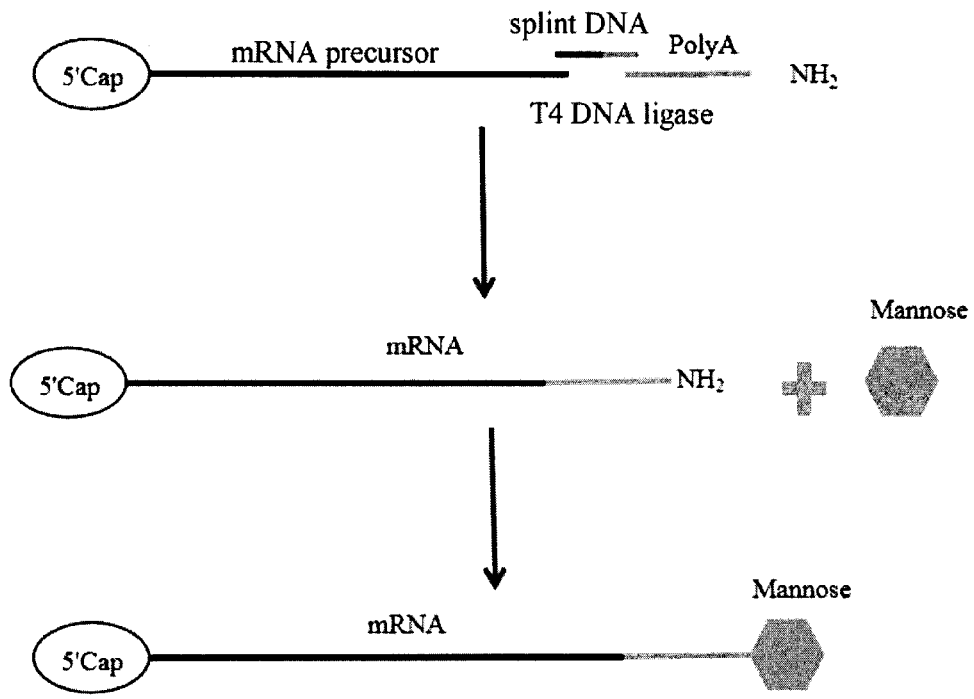
FIG. 3 is a schematic diagram showing the preparation process of the mRNA-mannose conjugate dependent on a "splint" DNA in an example of the preparation method of the mRNA composition according to the present invention (for linking a mannose in the terminal reaction)

In a preferred example, referring to FIG. 3, FIG. 3 is another approach of the preparation method of the mRNA composition in this example. The synthesized polyadenylic acid of which the 3' end is labeled with an amino group and the mRNA precursor are linked by the T4 DNA ligase to a splint DNA. The splint DNA contains a segment of base sequence at the 3' end of the mRNA precursor and a segment of base sequence at the 5' end of the polyadenylic acid, with the splint DNA acting as a bridge to link the mRNA precursor and the polyadenylic acid, and the link efficiency using the T4 DNA ligase is higher.

It will be appreciated that, in the example of the present invention, the ligase in the kit corresponding to the materials obtained from or used in the preparation method comprises a T4 DNA ligase, and the kit further comprises a splint DNA for linking the mRNA precursor and the polyadenylic acid.

Figure 4:
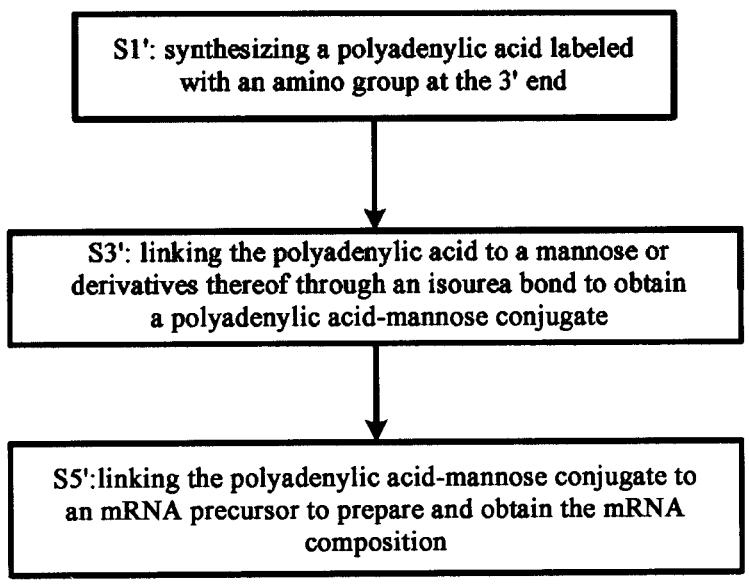
FIG. 4 is a schematic flow chart showing an example of the preparation method of the mRNA composition according to the present invention (for linking a mannose in the initiation reaction)

The present invention further presents a preparation method of an mRNA composition, see FIG. 4, comprising:

S1 synthesizing a polyadenylic acid labeled with an amino group at the 3'end;

S3', linking the polyadenylic acid to a mannose through an isourea bond to obtain a polyadenylic acid-mannose conjugate; and S5', linking the polyadenylic acid-mannose conjugate to the mRNA precursor to prepare and obtain the mRNA composition.

Specifically, the intermediate product of the preparation method is the polyadenylic acid-mannose conjugate, and at this time, a kit can be obtained, comprising: an mRNA precursor comprising a coding sequence encoding a specific protein; a conjugate of a polyadenylic acid with an amino group at the 3' end and a mannose; a ligase, the ligase being used for linking the mRNA precursor and the polyadenylic acid. The process of preparing the mRNA-mannose conjugate by the kit is also simpler and convenient to use.

Figure 5:
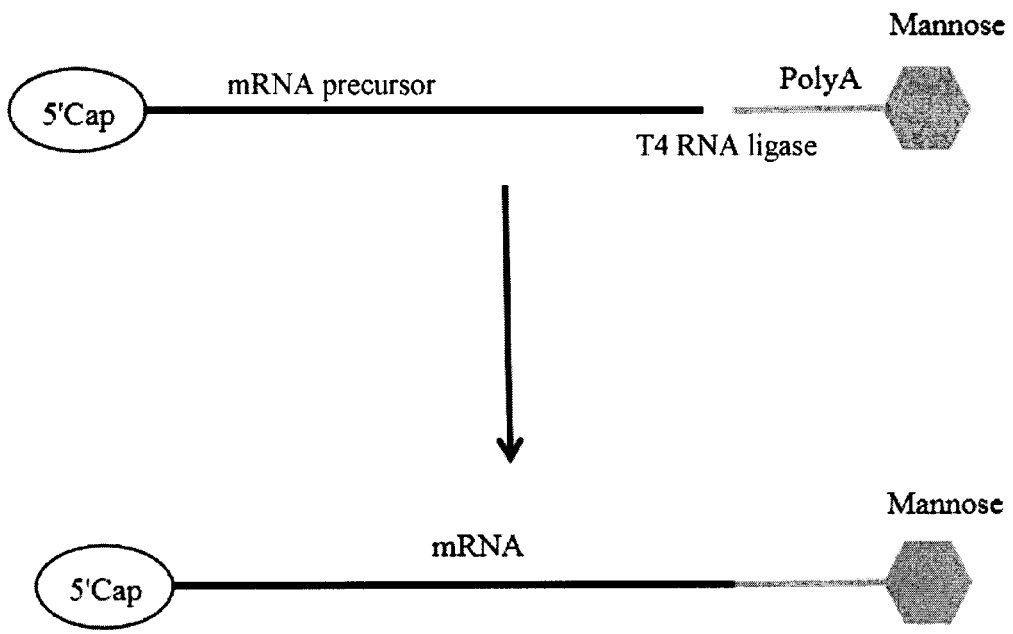
FIG. 5 is a schematic diagram showing the preparation process of the mRNA-mannose conjugates independent of a "splint" DNA in an example of the preparation method of the mRNA composition according to the present invention (for linking a mannose in the initiation reaction)
Figure 6:
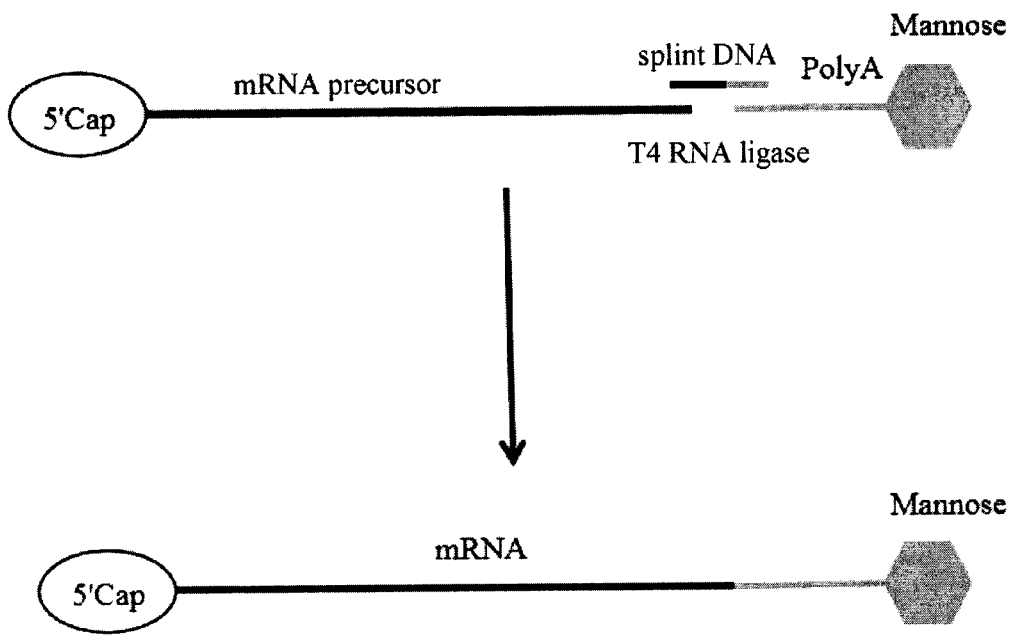
FIG. 6 is a schematic diagram showing the preparation process of the mRNA-mannose conjugates dependent on a "splint" DNA in an example of the preparation method of the mRNA composition according to the present invention (for linking a mannose in the initiation reaction)

Specifically, referring to FIG. 5, FIG. 5 is an approach of the preparation method of the mRNA composition in this example, showing that the polyadenylic acid-mannose conjugate and the mRNA precursor are linked by a T4 RNA ligase; referring to FIG. 6, FIG. 6 is another approach of the preparation method of the mRNA composition in this example, showing that the polyadenylic acid-mannose conjugate and the mRNA precursor are linked by a T4 DNA ligase to a splint DNA to improve the link efficiency.

It will be appreciated that, in the example of the present invention, the ligase in the kit corresponding to the materials obtained from or used in the preparation method can also be a T4 RNA ligase or a T4 DNA ligase. When the ligase in the kit is a T4 DNA ligase, the kit also comprises the splint DNA for linking the mRNA precursor and the polyadenylic acid-mannose conjugate.

The mRNA-mannose conjugates prepared in all the above-mentioned examples comprise: a mRNA encoding a polypeptide, the structure of the mRNA comprising at least one 5' cap structure, a 5' UTR with at least one Kozak sequence, a 3' UTR and a polyA tail, the mRNA being composed of uridine, cytidine, adenosine, guanosine and/or chemically modified nucleosides thereof, and the terminus of the mRNA being modified with at least one mannose. It will be appreciated that the mannose modification of the mRNA is not limited to the link of the mannose to the 3' end of the mRNA through an amino group, and other methods of linking the mannose to the terminus of the mRNA through methods such as enzymatic catalysis etc. also fall within the protection scope of the present invention.

Figure 7:
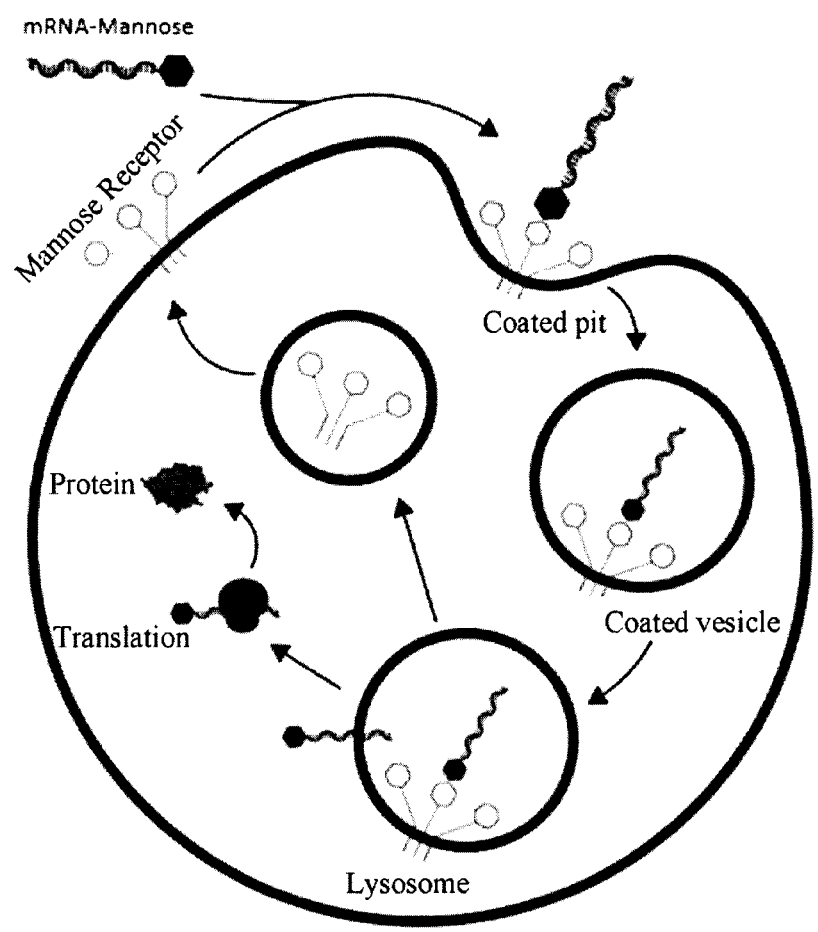
FIG. 7 is a schematic diagram showing the delivery process of the mRNA-mannose conjugate according to the present invention.

The mRNA-mannose conjugates obtained in the present invention are endocytosed into cells specifically expressing mannose receptors through the pathway as shown in FIG. 7 for translation. First, the extracellular mannose ligand binds to the mannose receptor on the membrane surface to form a ligand-receptor complex; the ligand-receptor complex laterally diffuses to form Clathrin-coated pits (coated pits) with the involvement of clathrin; then dynein induces the invagination of the cell membrane to form Clathrin-coated vesicles (coated vesicles); subsequently coated vesicles with clathrin removed fuse with lysosomes, the receptor dissociates from the ligand under the action of the proton sponge effect, and the mRNA-mannose conjugates enter cells and are translated into protein.

The present invention also provides an mRNA drug, comprising an mRNA-mannose conjugate. The mRNA-mannose conjugate can be prepared by any of the above-mentioned examples, or prepared by any of the above-mentioned kits. The mRNA drug may be a drug for treating tumors, or may be an mRNA vaccine or the like.

The present invention also provides a pharmaceutical composition, comprising an mRNA-mannose conjugate and a pharmaceutically acceptable excipient. The mRNA-mannose conjugate can be prepared by any of the above-mentioned examples, or prepared by any of the above-mentioned kits.

The present invention also provides a use of the mRNA-mannose conjugate or the above-mentioned pharmaceutical composition in the preparation of a medicament for expressing a target polypeptide in a mammalian subject. The mRNA-mannose conjugate can be prepared by any of the above-mentioned examples, or prepared by any of the above-mentioned kits.

The examples of the present invention achieved the coupling between an mRNA and a mannose, so that the mRNA can be targeted to specific cells through the mannose receptor. The method does not rely on physical methods and chemical transfection reagent methods, and is safe and effective.

The embodiments of the present invention will be described in detail below in conjunction with specific examples, but those skilled in the art will understand that the following examples are only used to illustrate the present invention and should not be regarded as limiting the scope of the present invention. Examples in which specific conditions are not specified are carried out according to the conventional conditions or conditions suggested by manufacturers. The reagents or instruments employed are all conventional products commercially available if the manufacturer is not indicated.

Example 1 Preparation of mRNA-Mannose Conjugate

The preparation process of the mRNA-mannose conjugate independent of a "splint" DNA, for linking the mannose in the terminal reaction:

1. Synthesis of Polyadenylic Acid

The target gene sequence was searched in the NCBI library according to the purpose, the corresponding vector sequence was designed, and the mRNA precursor sequence was obtained by in vitro transcription method. In addition, a polyadenylic acid tail sequence was synthesized by commercial sources and —NH2 was linked to the 3' end of the polyadenylic acid, the resulting polyadenylic acid is: 5'-AAAAAAAAAAAAAAAAAAAAAAAAAAAAAA-NH2-3' (SEQ ID NO: 1).

2. Synthesis of Mature mRNA

The T4 RNA ligase was used to link the above-mentioned 5'-AAAAAAAAAAAAAAAAAAAAAAAAAAAAAA-NH2-3' (SEQ ID NO: 1) to the 3' end of the mRNA precursor to form an mRNA with an amino group labeled at the 3' end: mRNA-NH2.

3. Synthesis of mRNA-mannose conjugate

In the sodium bicarbonate solution at pH 9.0, adding 200 µg (1 µg/µl, about 32 nmol) of mRNA-NH$_2$ and 100 µg (1 µg/µl, about 32 nmol) of 4-isothiocyanatophenyl-α-D-mannoside with a purity of ≥95%, followed by reacting the mixture overnight at 25° C. After the reaction stopped, the α-D-mannose was covalently bonded to the 3' end of the above-mentioned mRNA-NH$_2$ through an isourea bond to obtain an mRNA-mannose conjugate. After the completion of the reaction, the unreacted mRNA-NH$_2$ and 4-isothiocyanatophenyl-α-D-mannose were removed by purification using a desalting column (MWCO 7 kDa).

Example 2

The preparation process of the mRNA-mannose conjugate dependent on a "splint" DNA, for linking the mannose in the terminal reaction:

1. Synthesis of Polyadenylic Acid

The target gene sequence was searched in the NCBI library according to the purpose, the corresponding vector sequence was designed, and the mRNA precursor sequence was obtained by in vitro transcription method. In addition, a polyadenylic acid tail sequence was synthesized by commercial sources and —NH2 was linked to the 3' end of the polyadenylic acid, the resulting polyadenylic acid is: 5'-AAAAAAAAAAAAAAAAAAAAAAAAAAAAAA-NH2-3' (SEQ ID NO: 1).

2. Synthesis of Splint DNA

The splint DNA fragment was designed and synthesized by commercial sources, the sequence of which consists of two parts, comprising: a. a sequence part complementary to the 3' end sequence of the target gene sequence; b. a part complementary to the polyadenylic acid tail sequence.

3. Synthesis of Mature mRNA

The T4 DNA ligase was used to link the above-mentioned 5'-AAAAAAAAAAAAAAAAAAAAAAAAAAAAAA-NH2-3' (SEQ ID NO: 1) to the 3' end of the mRNA precursor under the mediation of a splint DNA fragment to form an mRNA of which the 3' end is labeled with an amino group: mRNA-NH2.

4. Synthesis of mRNA-Mannose Conjugate

In the sodium bicarbonate solution at pH 9.0, adding 200 µg (1 µg/µl, about 32 nmol) of mRNA-NH$_2$ and 100 µg (1 µg/µl, about 32 nmol) of 4-isothiocyanatophenyl-α-D-mannoside with a purity of ≥95%, followed by reacting the mixture overnight at 25° C. After the reaction stopped, covalently bonding the α-D-mannose to the 3' end of the above-mentioned mRNA-NH$_2$ through an isourea bond to obtain an mRNA-mannose conjugate. After the completion of the reaction, the splint DNA fragment was removed using a DNase, and purifying the products by using a desalting column (MWCO 7 kDa).

Example 3

The preparation process of the mRNA-mannose conjugates independent of a "splint" DNA, for linking the mannose in the initiation reaction:

1. Synthesis of Polyadenylic Acid

The target gene sequence was searched in the NCBI library according to the purpose, the corresponding vector sequence was designed, and the mRNA precursor sequence was obtained by in vitro transcription method. In addition, a polyadenylic acid tail sequence was synthesized by commercial sources and —NH2 was linked to the 3' end of the polyadenylic acid, the resulting polyadenylic acid is: 5'-AAAAAAAAAAAAAAAAAAAAAAAAAAAAAA-NH2-3' (SEQ ID NO: 1).

2. Synthesis of Polyadenylic Acid Tail Sequence-Mannose Conjugate

In the sodium bicarbonate solution at pH 9.0, adding 20 µg (1 µg/µl, about 32 nmol) of polyA-NH$_2$ and 100 µg (1 µg/µl, about 32 nmol) of 4-isothiocyanatophenyl-α-D-mannoside with a purity of ≥95%, followed by reacting the mixture overnight at 25° C. After the reaction stopped, covalently bonding the α-D-mannose to the 3' end of the above-mentioned polyA-NH$_2$ through an isourea bond to obtain an polyA-mannose conjugate. After completion of the reaction, the unreacted polyA-NH$_2$ and 4-isothiocyanatophenyl-α-D-mannose were removed by purification using a desalting column (MWCO 7 kDa).

3. Synthesis of Mature mRNA-Mannose Conjugate

The T4 RNA ligase was used to link the above-mentioned polyA-mannose to the 3' end of the mRNA precursor to obtain an mRNA-mannose conjugate. After the completion of the reaction, purification was performed using a desalting column (MWCO 7 kDa).

Example 4

The preparation process of the mRNA-mannose conjugates dependent on a "splint" DNA, for linking the mannose in the initiation reaction:

1. Synthesis of Polyadenylic Acid

The target gene sequence was searched in the NCBI library according to the purpose, the corresponding vector sequence was designed, and the mRNA precursor sequence was obtained by in vitro transcription method. In addition, a polyadenylic acid tail sequence was synthesized by commercial sources and —NH2 was linked to the 3' end of the polyadenylic acid, the resulting polyadenylic acid is: 5'-AAAAAAAAAAAAAAAAAAAAAAAAAAAAAA-NH2-3' (SEQ ID NO: 1).

2. Synthesis of Polyadenylic Acid Tail Sequence-Mannose Conjugate

In the sodium bicarbonate solution at pH 9.0, adding 20 µg (1 µg/µl, about 32 nmol) of polyA-NH$_2$ and 100 µg (1

μg/μl, about 32 nmol) of 4-isothiocyanatophenyl-α-D-mannoside with a purity of ≥95%, followed by reacting the mixture overnight at 25° C. After the reaction stopped, covalently bonding the α-D-mannose to the 3' end of the above-mentioned polyA-NH$_2$ through an isourea bond to obtain an polyA-Mannose conjugate. After the completion of the reaction, the unreacted polyA-NH$_2$ and 4-isothiocyanatophenyl-α-D-mannose were removed by purification using a desalting column (MWCO 7 kDa).

3. Synthesis of Splint DNA

The splint DNA fragment was designed and synthesized by commercial sources, the sequence of which consists of two parts, comprising: a. a sequence part complementary to the 3' end sequence of the target gene sequence; b. a part complementary to the polyadenylic acid tail sequence.

4. Synthesis of Mature mRNA-Mannose Conjugate

The T4 DNA ligase was used to link the above-mentioned polyA-mannose to the 3' end of the mRNA precursor under the mediation of a splint DNA fragment to obtain an mRNA-mannose conjugate. After the completion of the reaction, purification was performed using a desalting column (MWCO 7 kDa).

Example 5 Determination of Amino Group Content of mRNA-Mannose Conjugate

The amount of amino groups was determined by the fluorescamine method. Fluorosamine, which itself has no fluorescence properties, reacts with the primary amine to produce fluorescent substances. The amino group contained in mRNA-NH$_2$ is a primary amine. After mRNA-NH$_2$ was coupled with a mannose, the original primary amine became a secondary amine, so that the amount of —NH$_2$ in the conjugate of mRNA-NH$_2$ and mRNA-Mannose can be determined by the amount of fluorescence.

Figure 8:
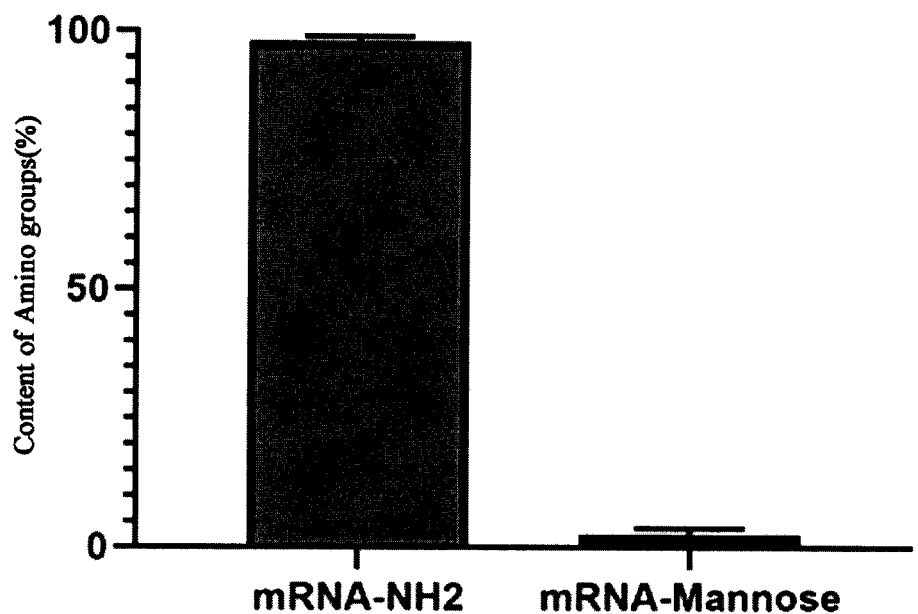
FIG. 8 is a graph showing the detection result of amino group content of the mRNA-mannose conjugate according to the present invention.

150 μg of the mRNA-Mannose conjugate synthesized in Example 1 was mixed with fluorescamine reagent in a 2 mg/mL acetone solution, and the mixture was incubated for 10 minutes, at a volume ratio of mRNA-Mannose conjugate to fluorescamine of 10:1. After completion of the incubation, the fluorescence intensity of the solution was measured with a fluorescence spectrophotometer (Gemini EMmicroplate reader, Molecular Device, CA, USA) at excitation wavelength and emission wavelength of 390 nm and 475 nm, respectively, and the amount of —NH$_2$ in the mRNA-mannose conjugate was calculated by using the fluorescence intensity of mRNA-NH$_2$ as the standard. The experimental results are shown in FIG. 8. As can be seen from the figure, the mRNA-mannose conjugate obtained in Example 1 hardly contains any detectable amino-NH$_2$, which proves that the linkage effect between mRNA and mannose is very good.

Example 6 Mass Spectrometry Analysis of mRNA-Mannose Conjugate

Figure 9:
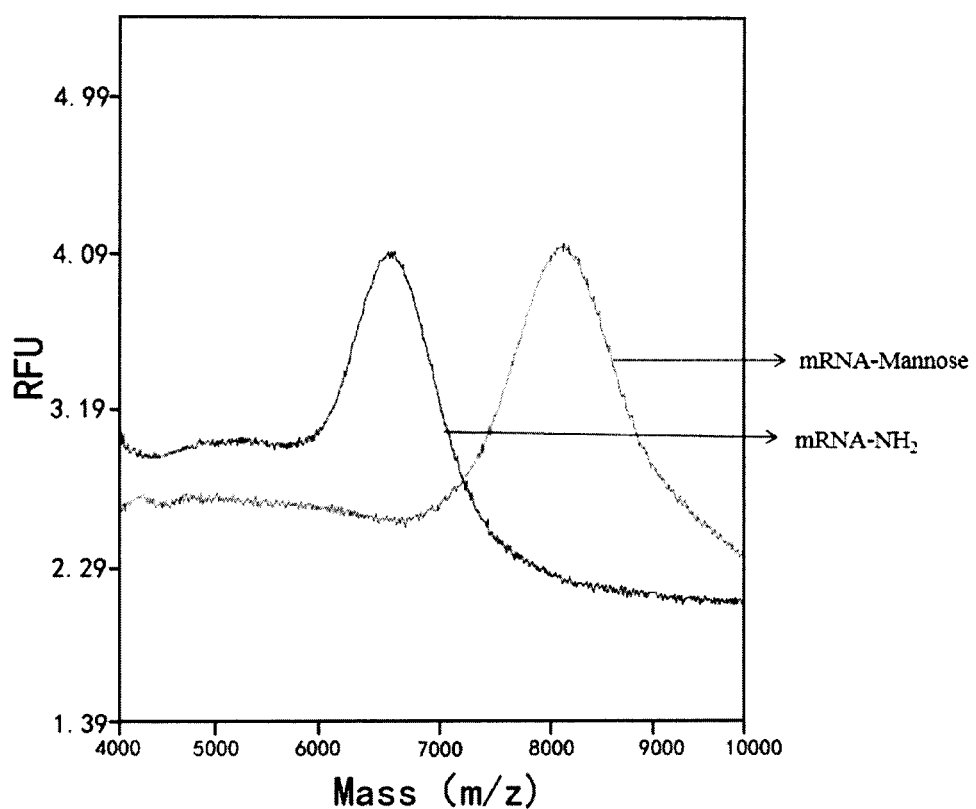
FIG. 9 is a graph showing the results of mass spectrometry analysis of the mRNA-mannose conjugate according to the present invention.

The dried mRNA-Mannose conjugate sample was mixed with 20,40,60-trihydroxyacetophenone (THAP) in a 70% acetonitrile (ACN)/0.1% trifluoroacetic acid (TFA) solution. The sample was analyzed by using MADI/MS (Ultraflextreme, Bruker, Germany) with smartbeam-IITM laser as ionization source. All spectra needed to be performed in positive mode with an ion source voltage of 25 kV, a repetition frequency of 1 kHz, and an average emission number of 5000. The experimental results are shown in FIG. 9, where mRNA-NH$_2$ is used as a control to indicate the position of the mRNA peak when mannose has not been linked. It can be seen from the figure that the preparation method of the present invention is able to efficiently prepare mRNA-Mannose conjugates, and there is no mRNA-NH$_2$ without linking to mannose, unconjugated mRNA, in the mRNA-Mannose conjugate.

Example 7 Intracellular Uptake Experiment of mRNA-Mannose Conjugate

Since there exists the mannose receptor CD206 in the phagolysosome, which can bind to the mRNA-mannose conjugate, the delivery of the mRNA-mannose conjugate inside the cell does not require complex intracellular pathways, namely macrophages are treated only with mRNA-mannose conjugates whereas without other carriers.

In order to determine whether the α-D-mannose in the mRNA-mannose conjugate can promote its internalization into macrophages, the fluorescently labeled mRNA and α-D-mannose were coupled together to obtain the fluorescently labeled mRNA-mannose conjugate (its preparation method is referred to Example 1, which is not repeated herein), which was then used to treat RAW264.7 cells (mouse mononuclear macrophage leukemia cells) for 24 h, and at the same time, as a control, the RAW264.7 cells were treated with fluorescently labeled mRNA-NH$_2$ for 24 hours, and after the treatment was completed, the number of fluorescent cells was detected by a flow cytometer.

Figure 10:
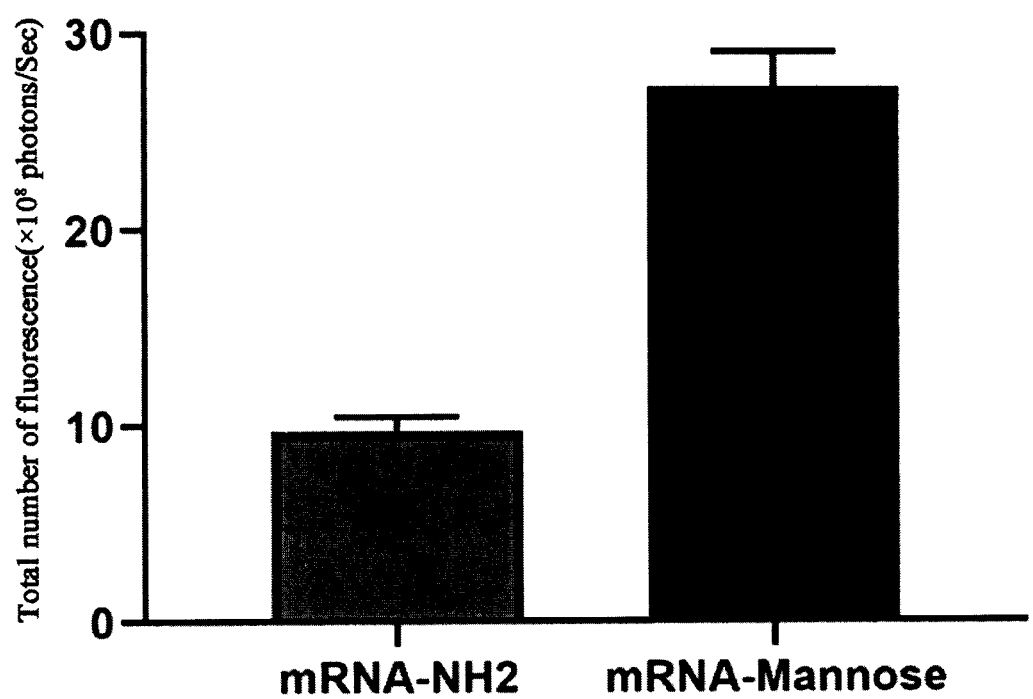
FIG. 10 is a graph showing the results of intracellular uptake experiment of the mRNA-mannose conjugate according to the present invention.

The experimental results are shown in FIG. 10, in which the total fluxes of fluorescent cells detected after treatment with mRNA-NH$_2$ and mRNA-mannose conjugates were 9.73±0.42 and 27.34±1.8, respectively. The number of fluorescence detected after the macrophages were treated with the fluorescently labeled mRNA-Mannose was much higher than that detected after the macrophages were treated with the fluorescently labeled mRNA-NH$_2$, which proves that the uptake amount of mRNA-mannose is much greater than that of mRNA-NH$_2$, and α-D-mannose can promote the internalization of mRNA-mannose conjugates into macrophages.

Example 8 Intracellular Uptake Competition Experiment of mRNA-Mannose Conjugate

Figure 11:
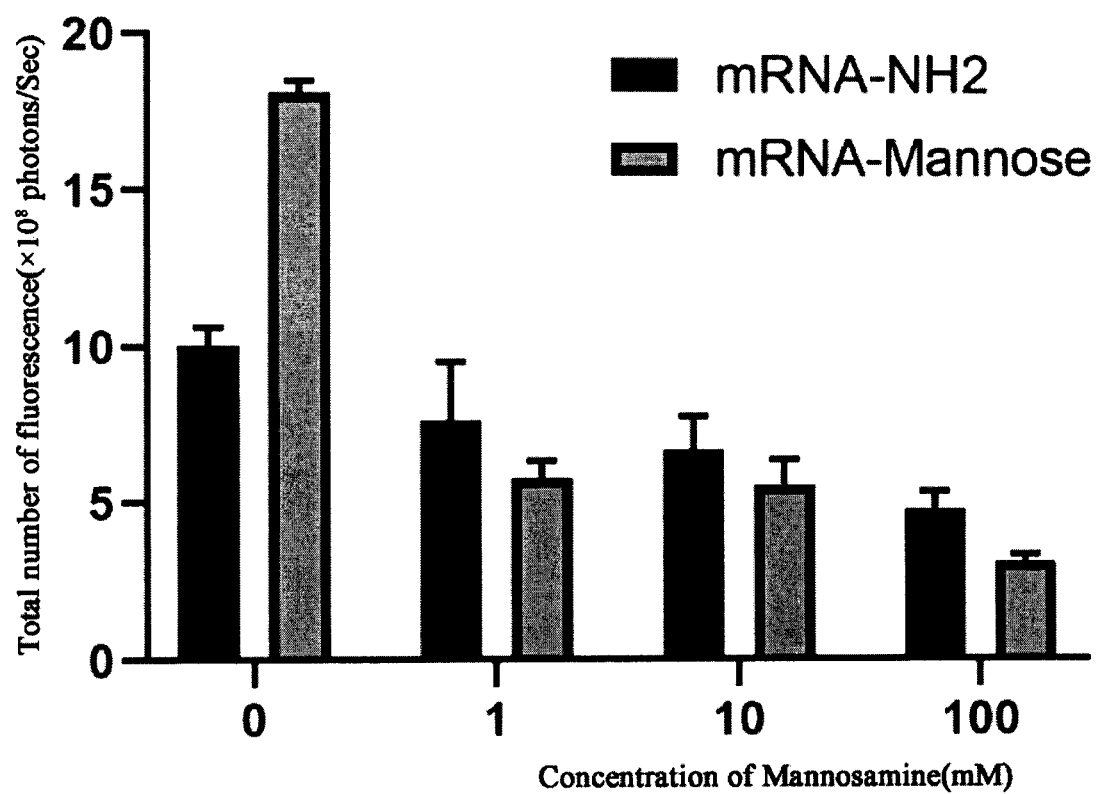
FIG. 11 is a graph showing the results of intracellular uptake competition experiment of the mRNA-mannose conjugate according to the present invention.

In order to verify that the uptake of mRNA-mannose conjugate into RAW264.7 cells is mediated by the mannose receptor CD206 in a mannose-specific manner, D-mannosamine was used to conduct a competitive uptake assay in RAW264.7 cells. After pre-incubating RAW264.7 cells with D-mannosamine, the cells were treated with fluorescently-labeled mRNA-mannose conjugate for 1 hour, at the same time, fluorescently-labeled mRNA-NH$_2$ was used as a control, to thereby determine the flux of fluorescent cells. The assay results are shown in FIG. 11, in which the amount of mRNA-mannose conjugates in macrophages was gradually reduced by adding D-mannosamine. When the treatment concentration of D-mannosamine was 1, 10 and 100 mM, the total flux of fluorescent cells decreased significantly. However, the uptake of mRNA-NH$_2$ into macrophages did not decrease significantly due to the addition of D-mannosamine. This result clearly shows that the mRNA-Mannose conjugate is taken up by RAW264.7 cells through mannose receptor-mediated endocytosis.

Example 9 Targeted Delivery Experiment of mRNA-Mannose Conjugate in Mice

Figure 12:
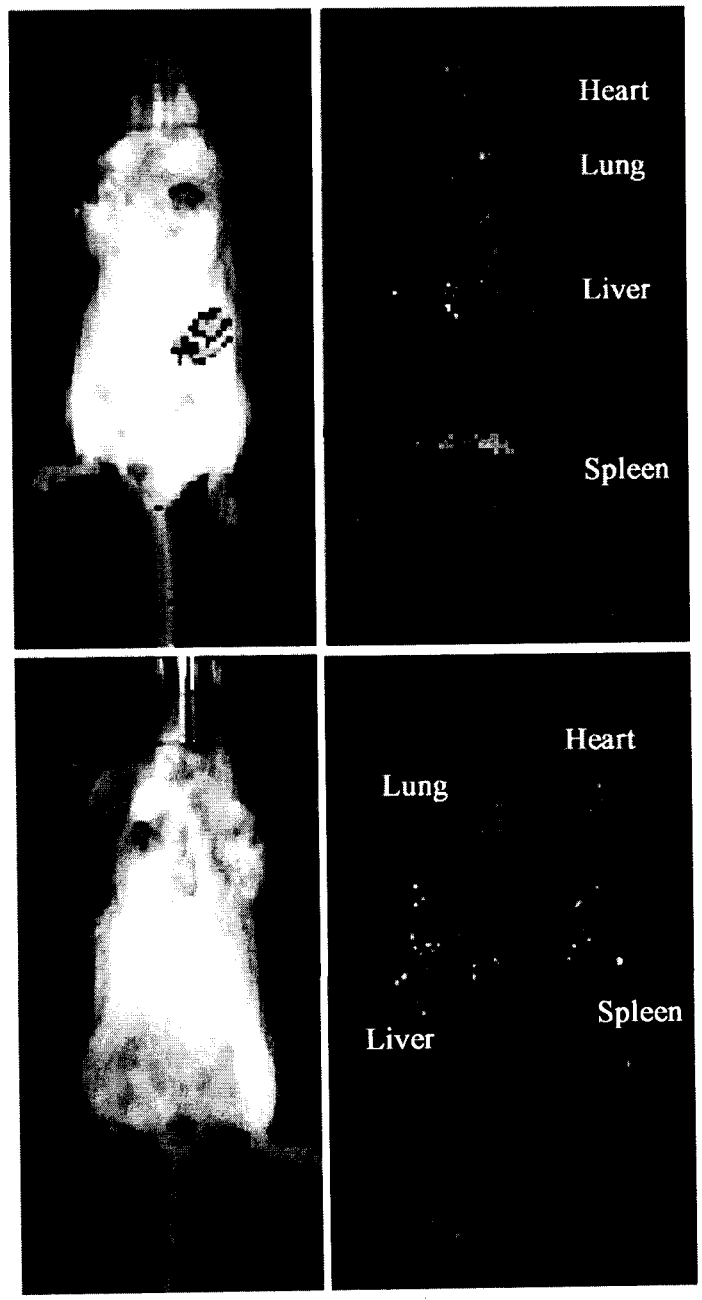
FIG. 12 is a graph showing the results of in vivo delivery experiment of the mRNA-mannose conjugate according to the present invention.

In order to determine the targetability of delivery of mRNA-mannose conjugates in mice after being endocytosed into cells, mRNA-mannose encoding luciferase was designed to be injected intravenously into mice, and the mRNA-NH$_2$ encoding luciferase was used as a control. 24 hours later, the mice were intraperitoneally injected with luciferin, a luciferase substrate, then fluorescence can be observed at sites with high expression of luciferase. The results indicate that, as shown in FIG. 12, the spleen is the main target organ for mRNA-mannose.

Figure 13:
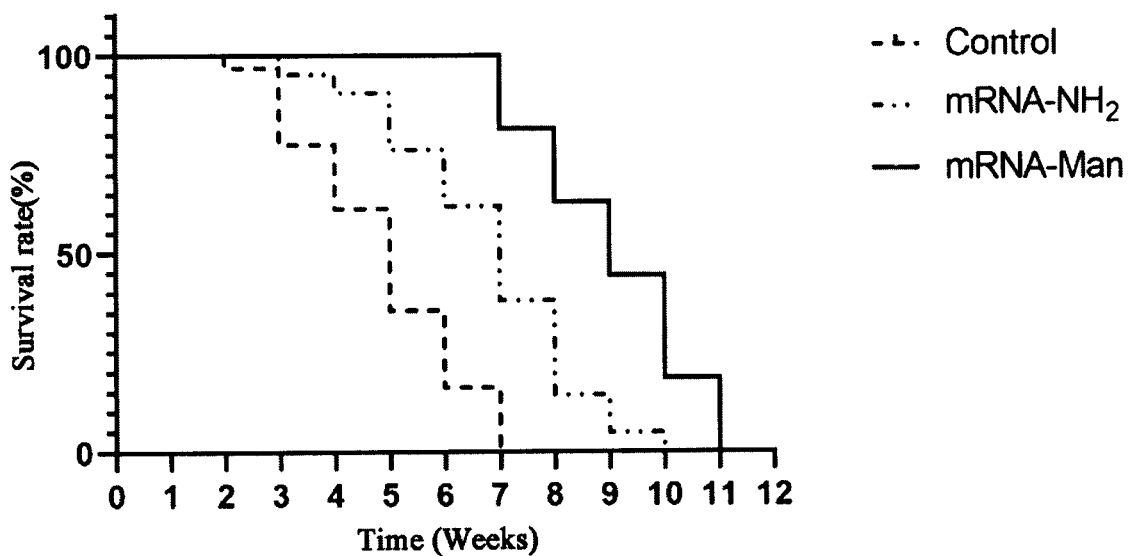
FIG. 13 is a graph showing experimental results of the effect of the mRNA-mannose conjugate on the survival rate in mice according to the present invention.

Example 10 Experiment on the Effect of mRNA-Mannose Vaccine on the Survival of Mice In order to compare the anti-tumor effects of mRNA-mannose conjugate (mRNA-Man) and mRNA monomer (mRNA-NH$_2$) encoding PD-1 antibody, a survival rate experiment of tumor-bearing mice was designed. The PD-1 antibody binds to the PD-1 protein on the surface of immune cells, thereby blocking the binding of PD-1 to the PD-L1 protein on the surface of cancer cells, and then activating the activity of immune cells, therefore preventing tumor cells from immune escape, and finally being killed by immune cells. The experiment results are shown in FIG. 13, where the control is a blank control, besides, injection of PD-1 mRNA-Man and PD-1 mRNA-NH$_2$ significantly improves the survival rate of humanized mice bearing melanoma, and the survival rate of mice injected with PD-1 mRNA-mannose was significantly higher than that of mice injected with PD-1 mRNA-NH$_2$. This result clearly shows that the mRNA-Man conjugate encoding PD-1 antibody is more easily endocytosed into target cells after injection into mice, to express PD-1 antibody, thereby improving the survival rate of tumor-bearing mice.

Example 11 Stability Experiment of mRNA-Mannose Conjugate

Figure 14:
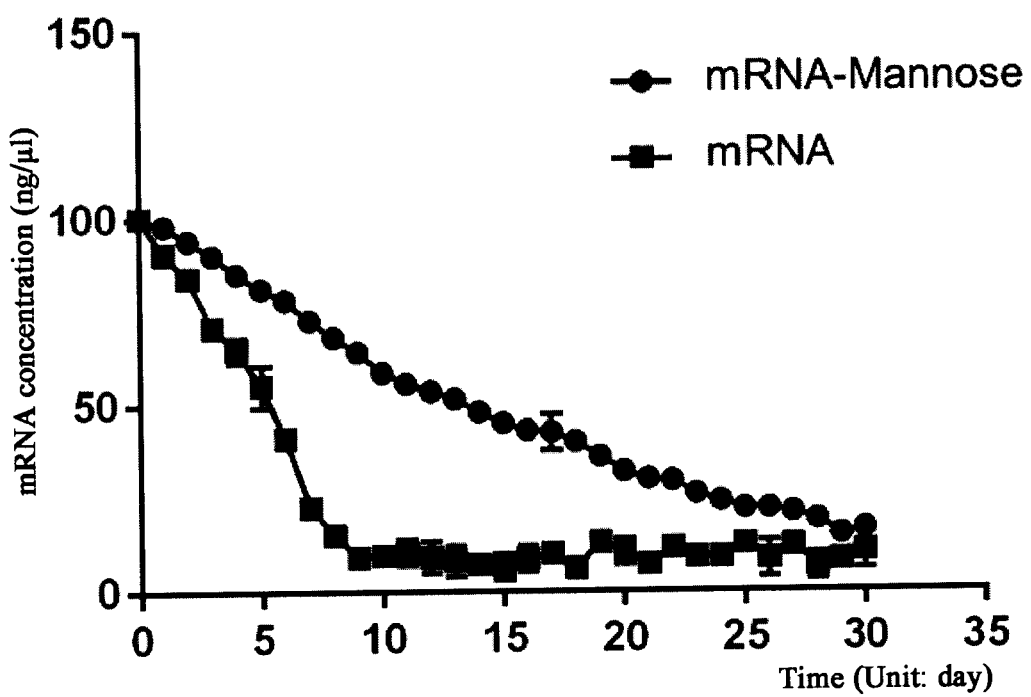
FIG. 14 is a graph showing experimental results of the stability of the mRNA-mannose conjugate according to the present invention.

To carry out the in vitro natural degradation experiment of mRNA, the PCR tube (Rnase free) containing mRNA (100 ng/µl) and mRNA-mannose (100 ng/µl) was put in a 37° C. incubator, the mRNA was collected and purified on day 1, 2, 3 ... 30, respectively, and the concentration was measured with NanoDrop ultra-micro spectrophotometer. The experimental results are shown in FIG. 14, the results indicate that the half-life of mRNA-Mannose can reach a range of 13 to 14 days, while the half-life of conventional mRNA is only in a range of 6 to 7 days, which proves that the mRNA-mannose conjugate is relatively stable.

The described above are only the preferred embodiments of the present invention. It should be noted that for those of ordinary skill in the art, several improvements and embellishments can be made without departing from the principle of the present invention, and these improvements and embellishments are also deemed to be within the scope of protection of the present invention.

What is claimed is:

1. An mRNA-mannose conjugate, comprising an mRNA encoding a polypeptide and at least one mannose attached to the mRNA via an amine at a 3' terminus of the mRNA, and wherein the mRNA comprises uridine, cytidine, adenosine, guanosine and/or chemically modified nucleosides thereof, wherein the amine is a secondary amine, and wherein the amine is formed on the last adenine of a polyA tail of mRNA.

2. The mRNA-mannose conjugate of claim 1, wherein the mRNA comprises at least one 5' cap structure, a 5' UTR, and/or a 3' UTR.

3. The mRNA-mannose conjugate of claim 2, wherein the at least one 5' cap structure is one or more selected from the group consisting of Cap0, Cap1, ARCA, inosine, N1-methyl-guanosine, 2'-fluoro-guanosine, 7-deaza-guanosine, 8-oxo-guanosine, 2-amino-guanosine, LNA-guanosine, 2-azido-guanosine, 7-methyl-guanosine-5'-triphosphate-5'-adenosine, guanosine-5'-triphosphate-5'-adenosine, 7-methyl-guanosine-5'-triphosphate-5'-guanosine, guanosine-5'-triphosphate-5'-guanosine and 7-methyl-guanosine-5'-triphosphate-5'-2-methoxyadenine-guanosine.

4. The mRNA-mannose conjugate of claim 2, wherein the 5' UTR comprises at least one Kozak sequence.

5. The mRNA-mannose conjugate of claim 1, wherein the chemically modified nucleoside is one or more selected from the group consisting of pyridin-4-one ribonucleoside, 5-aza-uridine, 2-thio-5-aza-uridine, 2-thiouridine, 4-thiopseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyl uridine, 1-taurinomethyl-pseudouridine, 5-taurinomethyl-2-thio-uridine, 1-taurinomethyl-4-thio-uridine, 5-methyl-uridine, 1-methyl pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, N4-acetylcytidine, 5-formyl cytidine, N4-methyl cytidine, 5-hydroxymethyl cytidine, 1-methyl pseudoisocytidine, pyrrolo-cytidine, pyrrolo-pseudoisocytidine, 2-thiocytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine-methyladenosine, N6-methyladenosine, N6-isopentenyladenosine, N6-(cis-hydroxyisopentenyl)adenosine, 2-methylthio-N6-(cis-hydroxyisopentenyl)adenosine, N6-glycylcarbamoyladenosine, N6-threonylcarbamoyladenosine, 2-methylthio-N6-threonylcarbamoyladenosine, N6,N6-dimethyladenosine, 7-methyladenine, 2-methylthio-adenine, 2-methoxy-adenosine, inosine, 1-methyl-inosine, Y nucleoside, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine and N2,N2-dimethyl-6-thio-guanosine.

6. The mRNA-mannose conjugate of claim 1, wherein the polypeptide is a therapeutic peptide.

7. The mRNA-mannose conjugate of claim 6, wherein the polypeptide comprises an antigen to a disease causing agent, or wherein the polypeptide comprises an immunomodulatory agent.

8. The mRNA-mannose conjugate of claim 7, wherein the disease causing agent is a tumor or a pathogen.

9. The mRNA-mannose conjugate of claim 7, wherein the polypeptide comprises the immunomodulatory agent, and wherein the immunomodulatory agent is a PD-1 antibody that binds to the PD-1 protein.

10. A pharmaceutical composition comprising the mRNA-mannose conjugate of claim 1 and a pharmaceutically acceptable excipient.

* * * * *